United States Patent [19]

Nagano et al.

[11] 4,438,115
[45] Mar. 20, 1984

[54] COMPOSITIONS AND METHODS FOR TREATING DISEASES IN CIRCULATORY ORGANS

[75] Inventors: Hiroyuki Nagano; Mitiro Takagi; Noboru Kubodera, all of Saitama; Isao Matsunaga, Tokyo; Tamotsu Yamazaki, Saitama; Hiroyuki Nabata, Tokyo; Kazushige Sakai, Tokyo; Shun-ichi Hata, Kanagawa, all of Japan

[73] Assignee: Chugai Seiyaku Kabushiki Kaisha, Tokyo, Japan

[21] Appl. No.: 272,077

[22] Filed: Jun. 10, 1981

[30] Foreign Application Priority Data

Jun. 13, 1980 [JP] Japan ................................. 55-79043

[51] Int. Cl.³ ........................................... A01N 43/48
[52] U.S. Cl. ................................................. 424/250
[58] Field of Search ........................ 544/392; 424/250

[56] References Cited

U.S. PATENT DOCUMENTS 2,922,788  1/1960  Parcell ................................. 544/392

FOREIGN PATENT DOCUMENTS 33-6468  3/1958  Japan ................................. 544/392

OTHER PUBLICATIONS

Chemical Abstracts, vol. 86, (1977), Par. 89,886q.

Primary Examiner—Elbert L. Roberts
Attorney, Agent, or Firm—Browdy & Neimark

[57] ABSTRACT

An agent for treating diseases in circulatory organs which comprises a piperazine compound of the formula

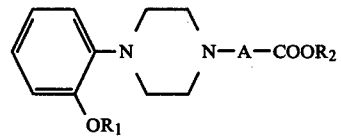

wherein $R_1$, $R_2$ and A are as defined hereunder, or a salt thereof and a pharmaceutically acceptable carrier.

15 Claims, 3 Drawing Figures

COMPOSITIONS AND METHODS FOR TREATING DISEASES IN CIRCULATORY ORGANS

The present invention relates to an agent for treating diseases in circulatory organs.

In a search for effective agents for treating diseases in circulatory organs, the present inventors have synthesized and screened many compounds and found that certain phenylpiperazine derivatives have not only great hypotensive action but also the desired effect to improve circulatory disorders. Based on this finding, these studies have continued in order to finally accomplish the present invention which is described hereunder.

Therefore, the present invention provides an agent for treating diseases in circulatory organs which contains as an effective ingredient a phenylpiperazine derivative of the formula:

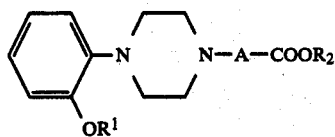

(I)

(wherein $R_1$ is a lower alkyl group having 1-6, preferably 1-4, carbon atoms; $R_2$ is a hydrogen atom or a lower alkyl group having 1-6, preferably 1-4, carbon atoms; and A is a straight or branched alkylene having 4-12, preferably 4-10, carbon atoms) or a salt thereof.

A compound of the formula (I) wherein $R_1$ is $CH_3$; $R_2$ is $C_2H_5$; and A is —$(CH_2)_4$— is known and described in Japanese Patent Publication No. 6468/58. In this prior art reference, the pharmacological action of the compound, ethyl 4-(o-methoxyphenyl)-1-piperazine valerate (4-(o-methoxyphenyl)-1-(4-ethoxycarbonylbutyl)piperazine), is not described at all, and instead, it is described as a compound which is reduced to form 4-(o-methoxyphenyl)-1-piperazine pentanol (4-(o-methoxylphenyl)-1-(5-hydroxypentyl)piperazine). According to the reference, the resulting alcohol compound is effective for treating hypertension, anxiety neurosis and other diseases. However, the present studies have shown that the compound of the present invention, namely, the starting material for preparing the compound described in Japanese Patent Publication No. 6468/58, has better pharmacological effects than the compound produced. The present invention is based on such unexpected finding.

Figure 1:
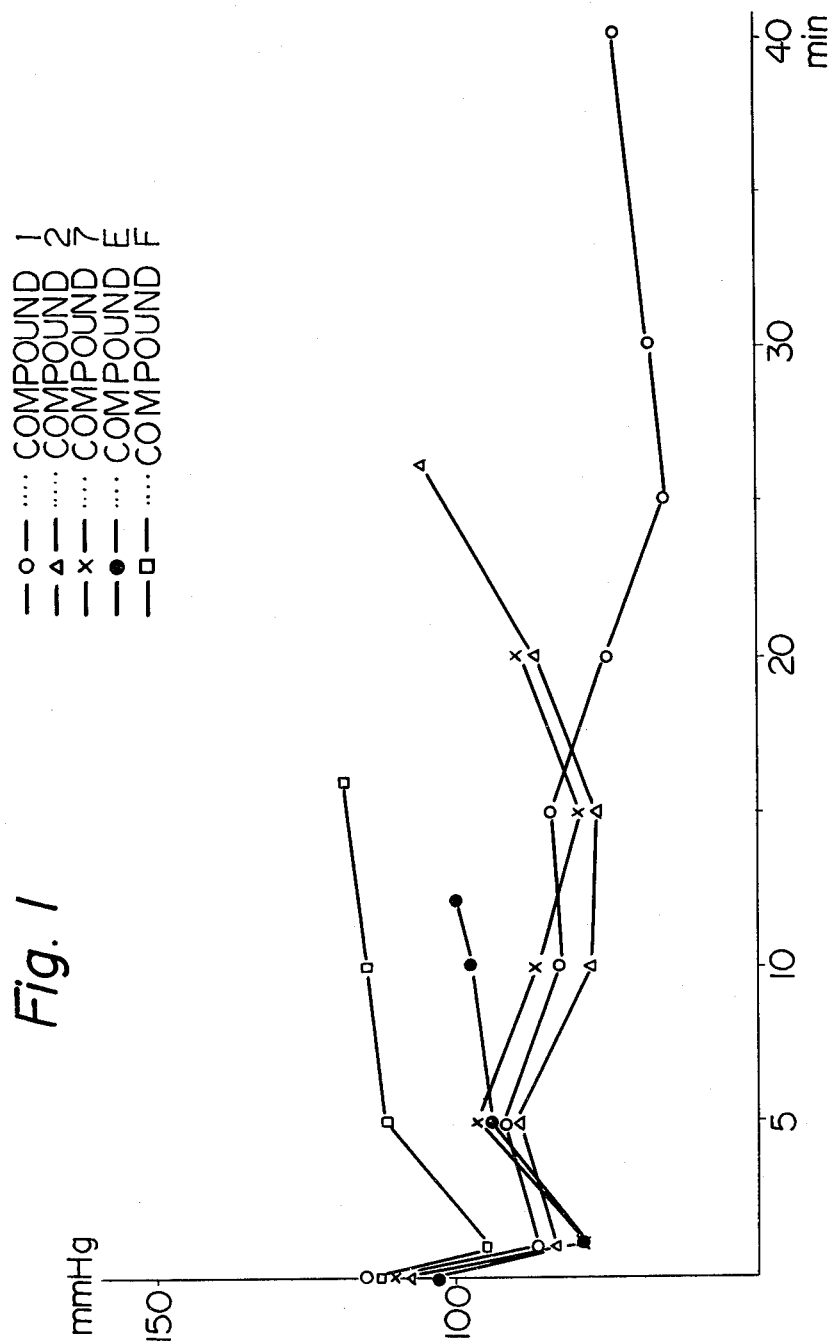
FIG. 1 is a graph showing the data of pressure reduction achieved in Experiment 2 described hereunder.

The compound of the present invention is prepared by various methods some of which are described in the following Preparations. The Preparations are identified by numbers that correspond to the respective numbers of compounds listed in the Experiments, Examples and other parts of the present specification.

PREPARATION 1

Synthesis of 1-(6-ethoxycarbonylhexyl)-4-(o-methoxyphenyl)piperazine and dihydrochloride thereof:

A mixture of 19.2 g (0.1 mol) of o-methoxyphenylpiperazine, 23.7 g (0.1 mol) of ethyl 7-bromoheptanoate and 20 ml of triethylamine was dissolved in 200 ml of benzene and the solution was heated under reflux for 4 to 6 hours. The insoluble precipitate was filtered off and the benzene solution was washed sequentially with a saturated aqueous solution of sodium bicarbonate and saturated brine, dried over anhydrous sodium sulfate, and the solvent was distilled off under vacuum. The resulting reddish brown oil was chromatographed on a silica gel (developing solvent: chloroform) to give 32.0 g of 1-(6-ethoxycarbonylhexyl)-4-(o-methoxyphenyl)piperazine as a pale yellow oil (yield=92%).

NMR (CDCl$_3$)δ: 1.23 (3H,t, J=7 Hz), 1.40(8H,br), 2.28 (4H,m), 3.11 (4H,m), 3.82 (3H,s), 4.10 (2H,q,J=7 Hz), 6.91 (4H,br.s), 2.60 (4H,m).

The obtained 1-(6-ethoxycarbonylhexyl)-4-(o-methoxyphenyl)piperazine was dissolved in 150 ml of ethanol and the solution was saturated with hydrogen chloride gas under cooling with ice. The solvent was distilled off under vacuum and the resulting crystalline residue was recrystallized from ethanol to give 36.6 g of colorless needles of 1-(6-ethoxycarbonylhexyl)-4-(o-methoxyphenyl)piperazine dihydrochloride having a melting point of 186°–189° C. (yield=87%).

Elemental analysis: Calculated for $C_{20}H_{32}N_2O_3 \cdot 2HCl$: C 57.00, H 8.13, N 6.65, Cl 16.83 (%). Found: C 56.86, H 8.14, N 6.53, Cl 16.95 (%).

PREPARATION 2

Synthesis of 1-(5-ethoxycarbonylpentyl)-4-(o-methoxyphenyl)piperazine and dihydrochloride thereof:

A mixture of 19.2 g (0.1 mol) of o-methoxyphenylpiperazine, 22.3 g (0.1 mol) of ethyl 6-bromocaproate and 20 ml of triethylamine in 200 ml of benzene was treated as in Preparation 1 to produce 30.1 g of 1-(5-ethoxycarbonylpentyl)-4-(o-methoxyphenyl)piperazine as a pale yellow oil (yield=90%).

NMR (CDCl$_3$)δ: 1.24 (3H,t,J=7 Hz), 1.50 (6H,br), 2.31 (4H,m), 2.65 (4H,m), 3.10 (4H,m), 3.84 (3H,s), 4.10 (2H,q,J=7 Hz), 6.95 (4H,br. s).

The obtained 1-(5-ethoxycarbonylpentyl)-4-(o-methoxyphenyl)piperazine was treated as in Preparation 1 to give 34.6 g of colorless needles of 1-(5-ethoxycarbonylpentyl)-4-(o-methoxyphenyl)piperazine dihydrochloride having a melting point of 177°–179° C. (yield=85%).

Elemental analysis: Calculated for $C_{19}H_{30}N_2O_3 \cdot 2HCl$: C 56.02, H 7.92, N 6.88, Cl 17.41 (%). Found: C 56.05, H 7.90, N 6.79, Cl 17.32 (%).

PREPARATION 3

Synthesis of 1-(6-ethoxycarbonylhexyl)-4-(o-isopropyloxyphenyl)piperazine and dihydrochloride thereof:

A mixture of 11.0 g (0.05 mol) of o-isopropyloxyphenylpiperazine, 11.85 g (0.05 mol) of ethyl 7-bromoheptanoate and 10 ml of triethylamine in 100 ml of toluene was treated as in Preparation 1 to form 16.0 g of 1-(6-ethoxycarbonylhexyl)-4-(o-isopropyloxyphenyl)piperazine as a pale yellow oil (yield=85%).

NMR (CDCl$_3$)δ: 1.25 (3H,t,J=7 Hz), 1.33 (6H,d,J=6 Hz), 1.50 (8H,br), 2.28 (4H,m), 2.53 (4H,m), 3.03

(4H,m), 4.03 (2H,q,J=7 Hz), 4.48 (1H,hep. J=6 Hz), 6.80 (4H,br. s).

The obtained 1-(6-ethoxycarbonylhexyl)-4-(o-isopropyloxyphenyl)piperazine was treated as in Preparation 1 to give 17.9 g of colorless needles of 1-(6-ethoxycarbonylhexyl)-4-(o-isopropyloxyphenyl)piperazine dihydrochloride having a melting point of 173°–174° C. (yield=80%).

Elemental analysis: Calculated for $C_{22}H_{36}N_2O_3 \cdot 2HCl$: C 58.79, H 8.52, N 6.23, Cl 15.78 (%). Found: C 58.79, H 8.57, N 6.23, Cl 15.84 (%).

PREPARATION 4

Synthesis of 1-(5-ethoxycarbonylpentyl)-4-(o-isopropyloxyphenyl)piperazine and dihydrochloride thereof:

A mixture of 11.0 g (0.05 mol) of o-isopropyloxyphenylpiperazine, 11.15 g (0.05 mol) of ethyl 6-bromocaproate and 10 ml of triethylamine in 100 ml of toluene was treated as in Preparation 1 to give 15.0 g of 1-(5-ethoxycarbonylpentyl)-4-(o-isopropyloxyphenyl)piperazine as a pale yellow oil (yield=83%).

NMR (CDCl$_3$)δ: 1.23 (3H,t,J=7 Hz), 1.32 (6H,d,J=7 Hz), 2.30 (4H,m), 2.60 (4H,m), 3.11 (4H,m), 4.11 (2H,q,J=7 Hz), 4.56 (1H, hept. J=6 Hz), 6.88 (4H,br. s).

The obtained 1-(5-ethoxycarbonylpentyl)-4-(o-isopropyloxyphenyl)piperazine was treated as in Preparation 1 to give 16.9 g of colorless needles of 1-(5-ethoxycarbonylpentyl)-4-(o-isopropyloxyphenyl)piperazine dihydrochloride having a melting point of 169°–170° C. (yield=78%).

Elemental analysis: Calculated for $C_{21}H_{34}N_2O_3 \cdot 2HCl$: C 57.93, H 8.33, N 6.43 (%). Found: C 57.77, H 8.26, N 6.46 (%).

PREPARATION 5

Synthesis of 1-(6-methoxycarbonylhexyl)-4-(o-methyoxyphenyl)piperazine and dihydrochloride thereof:

A mixture of 19.2 g (0.1 mol) of o-methoxyphenylpiperazine, 22.3 g (0.1 mol) of methyl 7-bromoheptanoate and 20 ml of triethylamine in 200 ml of benzene was treated as in Preparation 1 to give 31.1 g of 1-(6-methoxycarbonylhexyl)-4-(o-methoxyphenyl)piperazine as a pale yellow oil (yield=93%).

NMR (CDCl$_3$)δ: 1.40 (8H,br), 2.30 (4H,m), 2.62 (4H,m), 3.08 (4H,m), 3.63 (3H,s), 3.82 (3H,s), 6.91 (4H,br. s).

The obtained 1-(6-methoxycarbonylhexyl)-4-(o-methoxyphenyl)piperazine was dissolved in 150 ml of methanol and the solution was saturated with hydrogen chloride gas under cooling with ice. The solvent was distilled off under vacuum and the resulting crystalline residue was recrystallized from methanol to give 34.9 g of colorless needles of 1-(6-methoxycarbonylhexyl)-4-(o-methoxyphenyl)piperazine dihydrochloride having a melting point of 200°–201° C. (yield=86%).

Elemental analysis: Calculated for $C_{19}H_{30}N_2O_3 \cdot 2HCl$: C 56.02, H 7.92, N 6.88, Cl 17.41 (%). Found: C 56.08, H 7.88, N 6.82, Cl 17.30 (%).

PREPARATION 6

Synthesis of 1-(6-carboxylhexyl)-4-(o-methoxyphenyl)-piperazine:

A 16.7 g (0.05 mol) of 1-(6-methoxycarbonylhexyl)-4-(o-methoxyphenyl)piperazine obtained in Preparation 5 was dissolved in 50 ml of methanol, and the solution was mixed with 50 ml of 10% aqueous solution of sodium hydroxide. The mixture was stirred at room temperature for 2 hours. The solvent was distilled off under vacuum and cold methanol was added to the resulting residue. The insoluble matter was filtered off and the solvent was distilled off under vacuum. The resulting crystalline residue was recrystallized from water to give 13.6 g of colorless needles of 1-(6-carboxyhexyl)-4-(o-methoxyphenyl)piperazine having a decomposition point of 167.5° C. (yield=85%).

Elemental analysis: Calculated for $C_{18}H_{28}N_2O_3$: C 67.47, H 8.81, N 8.74 (%). Found: C 67.30, H 8.90, N 8.80 (%).

PREPARATION 7

Synthesis of 1-(4-ethoxycarbonylbutyl)-4-(o-methoxyphenyl)piperazine and dihydrochloride thereof:

A mixture of 19.2 g (0.1 mol) of o-methoxyphenylpiperazine, 20.9 g (0.1 mol) of ethyl 5-bromovalerate and 20 ml of triethylamine in 200 ml of toluene was treated as in Preparation 1 to give 27.2 g of 1-(4-ethoxycarbonylbutyl)-4-(o-methoxyphenyl)piperazine as a pale yellow oil.

The product was treated as in Preparation 1 to give colorless needles of 1-(4-ethoxycarbonylbutyl)-4-(o-methoxyphenyl)piperazine dihydrochloride having a melting point of 188°–190° C.

Elemental analysis: Calculated for $C_{18}H_{28}N_2O_3 \cdot 2HCl$: C 54.96, H 7.69, N 7.12, Cl 18.03 (%). Found: C 55.00, H 7.62, N 7.00, Cl 18.01 (%).

PREPARATION 8

Synthesis of 1-(4-ethoxycarbonylbutyl)-4-(o-isopropyloxyphenyl)piperazine and dihydrochloride thereof:

A mixture of 22.0 g (0.1 mol) of o-isopropyloxyphenylpiperazine, 20.9 g (0.1 mol) of ethyl 5-bromovalerate and 20 ml of triethylamine in 200 ml of toluene was treated as in Preparation 1 to give 30.0 g of 1-(4-ethoxycarbonylbutyl)-4-(o-isopropyloxyphenyl)piperazine as a pale yellow oil.

The product was treated as in Preparation 1 to give colorless needles of 1-(4-ethoxycarbonylbutyl)-4-(o-isopropyloxyphenyl)piperazine dihydrochloride having a melting point of 192°–193° C.

Elemental analysis: Calculated for $C_{20}H_{32}N_2O_3 \cdot 2HCl$: C 57.00, H 8.13, N 6.65, Cl 16.83 (%). Found: C 56.85, H 8.10, N 6.50, Cl 16.95 (%).

PREPARATION 9

Synthesis of 1-(6-ethoxycarbonyl-5-methylhexyl)-4-(o-methoxyphenyl)piperazine dihydrochloride:

A mixture of 9.6 g (0.05 mol) of o-methoxyphenylpiperazine, 12.6 g (0.05 mol) of ethyl 7-bromo-3-methylheptanoate and 10 ml of triethylamine was dissolved in 80 ml of toluene. The solution was heated gradually under reflux for 5 hours. After completion of the reaction, the precipitate was removed by filtration, and the filtrate was sequentially washed with a saturated solution of sodium bicarbonate and brine, and dried over magnesium sulfate and concentrated. The residue was dissolved in 100 ml of ethanol, saturated with hydrogen chloride gas, and concentrated. The crystalline residue was recrystallized from ethanol to give 14.9 g of 1-(6-ethoxycarbonyl-5-methylhexyl)-4-(o-methoxyphenyl)-piperazine dihydrochloride having a melting point of 190°–191° C.

Elemental analysis: Calculated for $C_{21}H_{34}N_2O_3.2HCl$: C 57.93, H 8.32, N 6.43, Cl 16.28 (%). Found: C 57.88, H 8.41, N 6.41, Cl 16.30 (%).

PREPARATION 10

Synthesis of 1-(5-ethoxycarbonyl-4-methylpentyl)-4-(o-methoxyphenyl)piperazine dihydrochloride:

A mixture of o-methoxyphenylpiperazine and ethyl 6-bromo-3-methylhexanoate was treated as in Preparation 9 to give 1-(5-ethoxycarbonyl-4-methylpentyl)-4-(o-methoxyphenyl)-piperazine dihydrochloride having a melting point of 170°–171° C.

Elemental analysis: Calculated for $C_{20}H_{32}N_2O_3.2HCl$: C 57.01, H 8.13, N 6.65, Cl 16.82 (%). Found: C 56.98, H 8.12, N 6.63, Cl 16.95 (%).

PREPARATION 11

Synthesis of 1-(6-ethoxycarbonylhexyl)-4-(o-methoxyphenyl)piperazine fumarate:

A solution of 3.48 g (0.01 mol) of the 1-(6-ethoxycarbonylhexyl)-4-(o-methoxyphenyl)piperazine in 50 ml of a mixture of ethyl acetate and ethanol (vol. ratio=50:1) was stirred with 1.16 g (0.01 mol) of fumaric acid at 60° C. for 30 minutes. The mixture was left to stand overnight under cooling to give 3.71 g of 1-(6-ethoxycarbonylhexyl)-4-(o-methoxyphenyl)piperazine fumarate. The fumarate was recrystallized from a mixture of ethyl acetate and ethanol (vol. ratio=50:1) to give an analytically pure fumarate having a melting point of 101°–102° C.

Elemental analysis: Calculated for $C_{20}H_{32}N_2O_3.C_4H_4O_4$: C 62.05, H 7.81 N 6.03 (%). Found: C 62.13, H 7.85, N 6.08 (%).

PREPARATIONS 12–15

The compounds identified in Table 1 below were prepared by repeating the procedure of Preparation 11.

Compounds 1, 2, 3, 5 and 7 of the present invention were checked by the following procedures:

1. Systemic blood pressure (SBP): The SBP was measured by a pressure transducer that was connected to a catheter inserted into the right femoral artery.
2. Heart rate (HR): The HR was measured by a cardiotachometer using the pulse wave of blood pressure as trigger pulse.
3. Common carotid artery blood flow (CaBF): The CaBF was measured with an electromagnetic flowmeter whose probe was put around the carotid artery.
4. Cerebral tissue blood flow (CTBF): The frontal cerebral lobe blood flow ($CTBF_1$) and lateral cerebral lobe blood flow ($CTBF_2$) were measured by the cross-thermocouple method.
5. Renal cortex blood flow (RTBF): The RTBF was measured by the cross-thermocouple method.

For some test compounds, their effect on the renal artery blood flow (RBF) was also investigated. The following compounds were used as controls.

A: hydralazine hydrochloride

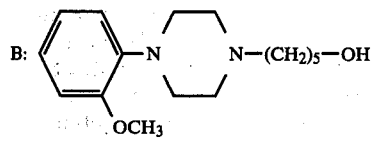

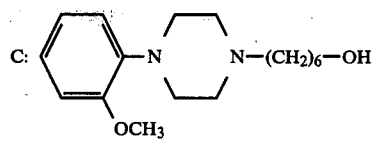

TABLE 1

| Preparation No. | Compound | Molecular formula | m.p. (°C.) | calculated (%) C | H | N | found (%) C | H | N |
|---|---|---|---|---|---|---|---|---|---|
| 12 | EMP*-tartrate | $C_{20}H_{32}N_2O_3.\frac{1}{2}C_4H_6O_6$ | 99–100 | 62.39 | 8.33 | 6.61 | 62.11 | 8.25 | 6.56 |
| 13 | EMP-maleate | $C_{20}H_{32}N_2O_3.C_9H_4O_4$ | 61–62 | 62.05 | 7.81 | 6.03 | 62.10 | 7.83 | 6.10 |
| 14 | EMP-monohydrochloride | $C_{20}H_{32}N_2O_3.HCl$ | 144–145 | 62.40 | 8.64 | 7.28 | 62.46 | 8.66 | 7.37 |
| 15 | EMP-fumarate | $C_{20}H_{32}N_2O_3.\frac{1}{2}C_4H_4O_4$ | 88 | 65.00 | 8.43 | 6.89 | 65.03 | 8.44 | 6.94 |

*EMP: 1-(6-ethoxycarbonylhexyl)-4-(o-methoxyphenyl)piperazine

EXPERIMENT 1

The acute toxicity of Compounds Preparation Nos. 1 to 15 was examined by the oral administration of them to male SD strain rats (five rats per group) for fourteen consecutive days. All compounds had low toxicity and none supressed weight gain. No rat died upon administration of Compound 1 or 2 (both as hydrochloride) in a dose of 400 mg/Kg.

EXPERIMENT 2

A beagle was anesthetized by intravenous injection of sodium pentobarbital and under artificial respiration an incision was made in the chest. The various actions of

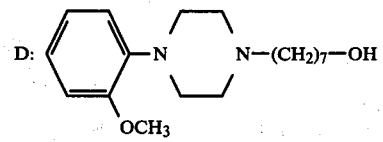

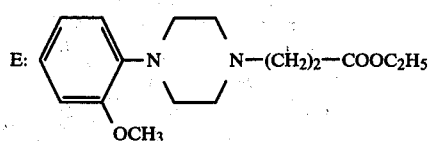

-continued

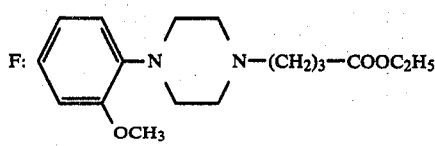

(a) Reduction of systemic blood pressure

Compounds 1, 2, 7, E and F were dissolved in physiological saline or distilled water and the solutions were administered to rats intravenously in a dose of 25 μg/kg. The resulting change in their systemic blood pressure is represented in FIG. 1. The effect of control compounds E and F to reduce the systemic blood pressure was only temporary but in the case of Compounds 1, 2 and 7 of this invention, the initial temporary reduction was followed by a reduction in the second phase, and the systemic blood pressure was maintained low thereafter.

The same experiment was conducted repeatedly with Compounds 1, 2, 3, 5, 7, B, C, D, E and F. The average percent reduction in blood pressure and the average period during which the blood pressure was maintained at reduced level are indicated in Tables 2 and 3. Neither table contains data for control compound A because an intranveous injection of the compound in a dose of 25 μg/Kg did not exhibit significant reduction in blood pressure. An shown in Table 3, Compound 1 maintained the blood pressure at low level for a longer period than did the others.

TABLE 2

| Compound | Average percent reduction |
| --- | --- |
| 1 | 25.51 |
| 2 | 22.40 |
| 3 | 22.05 |
| 5 | 23.14 |
| 7 | 19.06 |
| B | 16.14 |
| C | 12.64 |
| D | 14.30 |
| E | 15.05 |
| F | 15.23 |

TABLE 3

| Compound | Average low pressure retention time (min) |
| --- | --- |
| 1 | 47.3 |
| 2 | 20.0 |
| 3 | 22.4 |
| 5 | 18.6 |
| 7 | 13.4 |
| B | 15.0 |
| C | 14.4 |
| D | 22.5 |
| E | 6.8 |
| F | 8.8 |

(b) Change in heart rate

The effect of the test compounds and control compounds on the heart rate is shown in Table 4. Control compounds E and F first increased the heart rate and thereafter the increased heart rate gradually returned to the normal level. As for the compounds of the present invention, a temporary increase was followed by a gradual decrease which started almost at the same time when a second phase reduction in blood pressure occurred (see FIG. 1).

TABLE 4

| Compound | Percent change in heart rate |
| --- | --- |
| 1 | −9.6 |
| 2 | −1.6 |
| 3 | −4.0 |
| 5 | −2.2 |
| 7 | 13.2 |
| B | 9.9 |
| C | 8.1 |
| D | −9.1 |
| E | 16.8 |
| F | 11.2 |

(c) Change in left ventricular pressure

The compounds of the present invention decreased both the positive dp/dt and negative dp/dt of the left ventricular pressure although the decrease was temporary. In this respect, they differ from known beta-receptor blocking agents that decrease only the positive dp/dt.

(d) Cerebral tissue blood flow

The compounds of the present invention had a tendency to increase the cerebral tissue blood flow.

(e) Renal artery blood flow

The compounds of the present invention had a tendency to increase the renal artery blood flow following a temporary decrease.

(f) Renal cortex blood flow

In spite of the effect to reduce the systemic blood pressure, the compounds of the present invention did not change or increased the renal cortex blood flow.

(g) Effect on norepinephrine-induced response

The compounds of the present invention inhibited an increase in the systemic blood pressure and a temporal decrease in the renal blood flow induced by norepinephrine. This fact shows that the compounds of the present invention suppress the action of norepinephrine to stimulate alpha-receptors and beta-receptors.

EXPERIMENT 3

Figure 2:
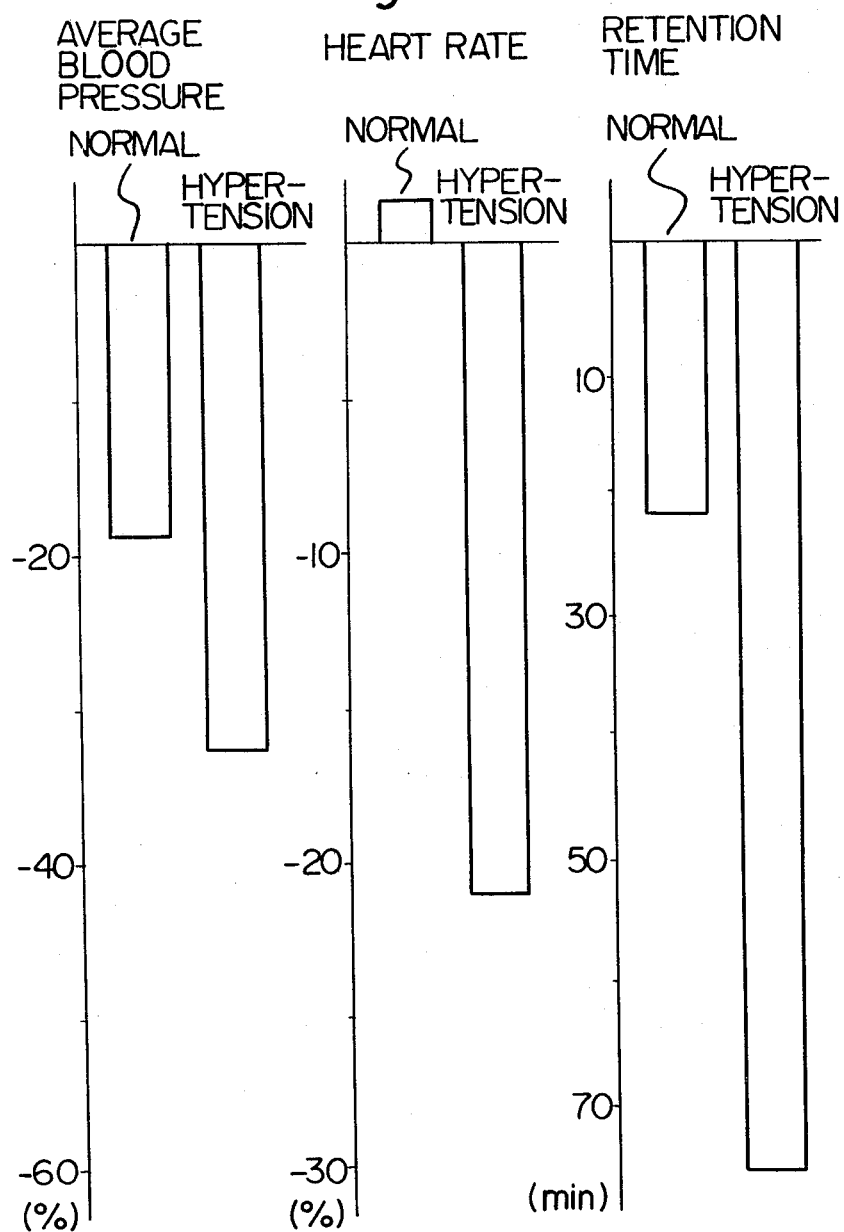
FIG. 2 is a graph showing the effectiveness of compound 1 (synthesized by Preparation 1) in reducing the systemic blood pressure of a hypertensive subject.
Figure 3:
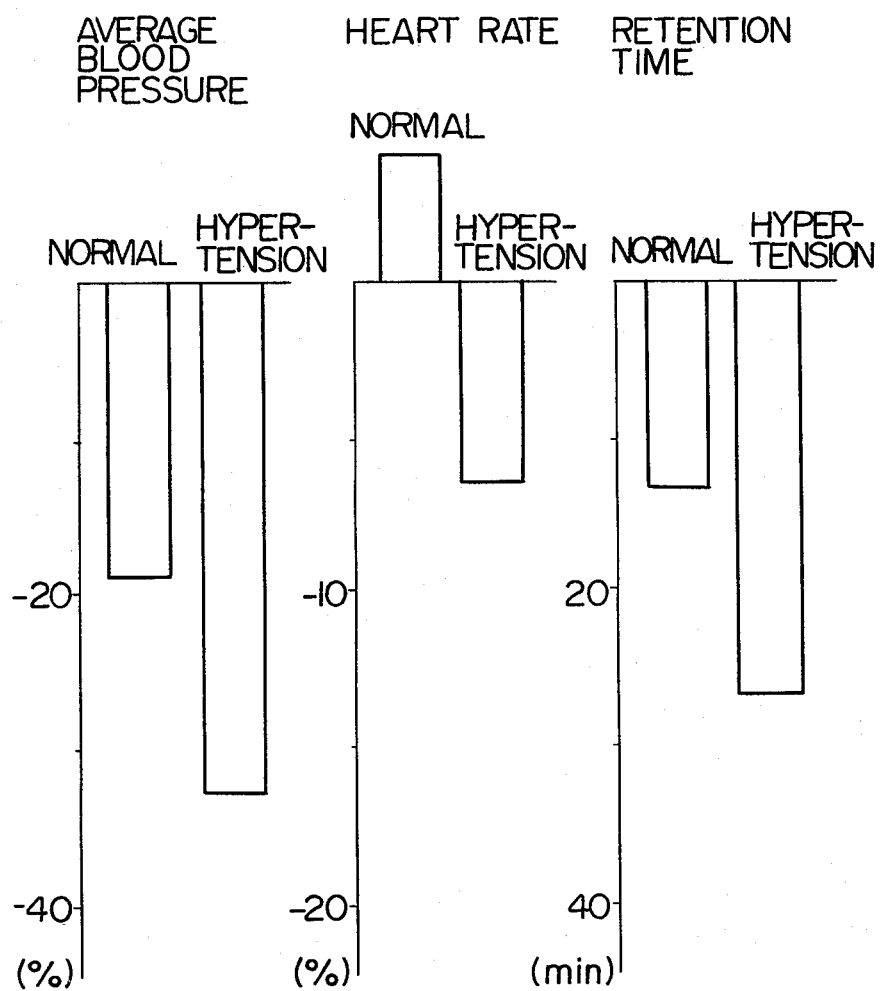
FIG. 3 is a graph showing the effectiveness of compound 2 (synthesized by Preparation 2) in reducing the systemic blood pressure of the hypertensive subject.

Hypertension was induced in a beagle by exciting the sympathetic nerve due to an obstruction of the bilateral vertebral artery and right common carotid artery, as well as a stricture of the left common carotid artery. The beagle was treated intravenously with 25 μg/Kg of Compounds 1 and 2. As shown in FIG. 2 (Compound 1) and FIG. 3 (Compound 2), the compounds were more effective in reducing the systemic blood pressure and heart rate and extending the low pressure retention time in the affected beagle than in a normal subject.

EXPERIMENT 4

Unanesthetized SHR rats (five rats per group) were administered orally 10 mg/Kg of Compound 1. The blood pressure which was 180±5.0 mmHg just before the administration fell by 127±11.6 mmHg one hour later, and by 137±7.6 mmHg two hours later, and it was maintained at the reduced level for a satisfactorily long time.

As demonstrated in the above experiments, the compounds of the present invention have desired effects on the circulatory system and are effective for treating various diseases in circulatory organs as hypotensive, medicine to treat ischemic cardiac diseases, and vasodilator for peripheral blood vessels such as cerebral vessels, limb vessels and renal vessels.

The compounds of the present invention can be administered to human beings orally or parenterally in a suitable form such as intramuscular injection, subcutaneous injection, intravenous injection or suppository.

When used as a medicine, the compounds of the present invention are formulated by conventional techniques into a tablet, slow release agent, powder, capsule, suspension, injection or suppository. To state more specifically, a tablet, granule or powder is prepared by mixing the compounds with a pharmaceutical carrier such as excipient, binder or solvent, e.g. lactose, starch, mannitol, sucrose, kaolin, crystalline cellulose, talc, calcium carbonate. A capsule is prepared by packing granules or a powder of the compounds in a hard capsule or filling a soft capsule with a solution of the compounds in oil. A suspension is prepared by suspending gum arabic powder, sucrose or the like in an aqueous solution of the compounds, followed by pH adjustment. An injection is prepared by mixing the compound with mannitol. The amount of the compounds contained in the respective formulations is such that they exhibit the ability to treat and prevent diseases in circulatory organs while inhibiting any undesired side effects.

It is convenient for oral administration that one tablet or capsule contain these compounds in a unit dosage of about 0.5 to 60 mg, and for parenteral administration, a unit dosage of about 0.1 to 10 mg per vial is convenient. The actual dose using the above unit dosage varies with the conditions of individual patients, and hence must be changed according to the requirements of the patients. A daily dose of from about 0.1 to 1000 mg may be administered per adult. A dose of about 1 to 50 mg is preferred since it is an amount that is safe and achieves the intended effect.

EXAMPLE 1

Tablet

An intimate mixture of the following ingredients was directly compressed by a tableting machine into tablets having a diameter of 7 mm and weighing 100 mg.

| Compound 11 | 2.5 parts (by weight) |
|---|---|
| Lactose | 52 parts |
| Corn starch | 20 parts |
| Crystalline cellulose | 25 parts |
| Magnesium stearate | 0.5 parts |

EXAMPLE 2

Hard capsule

An intimate mixture (200 mg) of the following ingredients were packed into a capsule No. 3 with a packer to form capsules containing 20 mg and 10 mg of the effective ingredient, respectively.

| (a) | Compound 1 (hydrochloride) | 20 parts (by weight) |
|---|---|---|
| | Lactose | 176 parts |
| | Magnesium stearate | 4 parts |
| (b) | Compound 1 (hydrochloride) | 10 parts |
| | Lactose | 186 parts |
| | Magnesium stearate | 4 parts |

EXAMPLE 3

Granule

An intimate mixture of the following ingredients was kneaded and shaped into granules 1 mm in size by a granulator.

| Compound 11 | 2.5 parts (by weight) |
|---|---|
| Lactose | 717.5 parts |
| Corn starch | 280 parts |

EXAMPLE 4

Injection

An intimate mixture of the following ingredients was put in an ampoule which was freeze-dried and fused in a known-manner. Prior to use, the lyophilized powder was reconstituted with 1 ml of distilled water.

| Compound 1 (dihydrochloride) | 1 mg |
|---|---|
| Mannitol | 50 mg |

What is claimed is:

1. A composition for treating diseases in circulatory organs which comprises a piperazine compound of the formula:

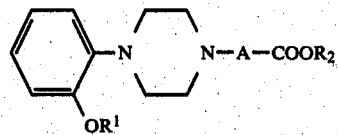

(wherein $R_1$ is a lower alkyl group; $R_2$ is a hydrogen atom or a lower alkyl; and A is a straight or branched alkylene) or a salt thereof and a pharmaceutically acceptable carrier selected from the group consisting of lactose, starch, mannitol, sucrose, kaolin, crystalline cellulose, talc, calcium carbonate and magnesium stearate.

2. A composition for treating diseases in circulatory organs which comprises a piperazine compound of the formula:

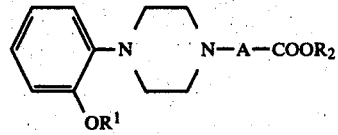

(wherein $R_1$ is a lower alkyl group; $R_2$ is a hydrogen atom or a lower alkyl group; and A is a straight or branched alkylene) or a salt thereof and a pharmaceutically acceptable carrier, wherein said composition is formulated into the form of a tablet, granule, powder, capsule or slow release agent for oral administration.

3. A composition according to claim 2 in unit dosage form, containing 0.5 to 60 mg of the piperazine compound or a salt thereof per unit dosage.

4. A composition for treating diseases in circulatory organs which comprises a piperazine compound of the formula:

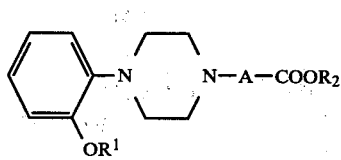

(wherein $R_1$ is a lower alkyl group; $R_2$ is a hydrogen atom or a lower alkyl group; and A is a straight or branched alkylene) or a salt thereof and a pharmaceutically acceptable carrier, wherein said composition is formulated into the form of an injection and wherein said carrier is mannitol.

5. A composition according to claim 4 in unit dosage form, containing 0.1 to 10 mg of the piperazine compound or a salt thereof per unit dosage.

6. A method for treating diseases in circulatory organs which comprises administering to a patient having such a disease an effective amount of a piperazine compound of the formula:

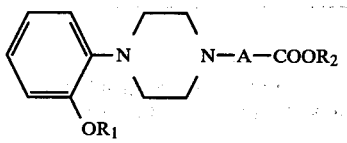

wherein $R_1$ is a lower alkyl group; $R_2$ is a hydrogen atom or a lower alkyl group; and A is a straight or branched alkylene) or a salt thereof.

7. A method in accordance with claim 6 wherein such disease is hypertension.

8. A method in accordance with claim 6 wherein such disease is ischemic cardiac disease.

9. A method in accordance with claim 6 wherein such disease is one treatable by an agent for vasodilating peripheral blood vessels.

10. A method in accordance with claim 6 wherein said piperazine is administered in an effective dosage of 0.1 to 1000 mg per day.

11. A method in accordance with claim 6 wherein said piperazine is administered in an effective dosage of 1 to 50 mg per day.

12. A composition for treating diseases in circulatory organs which comprises a piperazine compound of the formula:

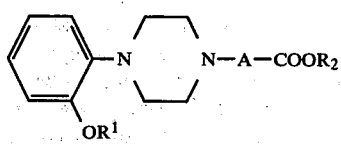

(wherein $R_1$ is a lower alkyl group; $R_2$ is a hydrogen atom or a lower alkyl group; and A is a straight-chain or branched alkylene having 4-12 carbon atoms) or a salt thereof and a pharmaceutically acceptable carrier.

13. A composition in accordance with claim 12 wherein $R_1$ is an alkyl group having 1-4 carbon atoms, $R_2$ is hydrogen or an alkyl group having 1-4 carbon atoms and A is a straight-chain or branched alkylene having 4-10 carbon atoms.

14. A method for treating diseases in circulatory organs which comprises administering to a patient having such a disease an effective amount of the composition in accordance with claim 12.

15. A method for treating diseases in circulatory organs which comprises administering to a patient having such a disease an effective amount of the composition in accordance with claim 13.

* * * * *